United States Patent [19]
Guan et al.

[11] Patent Number: 4,757,040
[45] Date of Patent: Jul. 12, 1988

[54] CLASS OF PILLARED INTERLAYERED CLAY MOLECULAR SIEVE PRODUCTS WITH REGULARLY INTERSTRATIFIED MINERAL STRUCTURE

[75] Inventors: Jingjie Guan; Enze Min; Zhiqing Yu, all of Beijing, China

[73] Assignee: Research Institute of Petroleum Processing Sinopec, Beijing, China

[21] Appl. No.: 840,688

[22] Filed: Mar. 18, 1986

[30] Foreign Application Priority Data

Apr. 1, 1985 [CN] China ................... 85100216

[51] Int. Cl.$^4$ .................. B01J 21/16; B01J 20/12
[52] U.S. Cl. ......................... 502/63; 502/80; 502/84
[58] Field of Search ............... 502/80, 84, 63

[56] References Cited

U.S. PATENT DOCUMENTS

| | | | |
|---|---|---|---|
| 4,176,090 | 11/1979 | Vaughan | 502/84 |
| 4,248,739 | 2/1981 | Vaughan | 502/84 |
| 4,417,090 | 11/1983 | Heinerman et al. | 502/80 |

FOREIGN PATENT DOCUMENTS

| | | | |
|---|---|---|---|
| 0145061 | 6/1985 | European Pat. Off. | |
| 2231644 | 12/1974 | France | |
| 2394324 | 1/1979 | France | |
| 85/02399 | 6/1985 | PCT Int'l Appl. | 502/80 |

OTHER PUBLICATIONS

Hydrothermal Stability Characteristics of a New Layer-Pillar Type Molecular Sieve—Article; Guan, J., Min, E., Yu, Z.
Journal of American Chemical Society 107; 2362, "High-Resolution Solid-State 27Al and 29Si Nuclear Resonance Study of Pillared Clays", (1985).
Journal of American Chemical Society, No. 12, 1983, p. 665, Synthesis and Catalytic Properties of Pillared Clay.

*Primary Examiner*—Carl F. Dees
*Attorney, Agent, or Firm*—Ladas & Parry

[57] ABSTRACT

A class of pillared interlayered clay molecular sieves with large pore size were prepared by cross-linking the regularly interstratified mineral clay. Wherein the cross-linked rectorites possess an extraordinary thermal and hydrothermal stabilities. Said class of pillared interlayered clay molecular sieves are potential commercial catalysts for carbonium-ion type reactions, adsorbents and catalyst carriers.

18 Claims, 4 Drawing Sheets

CLASS OF PILLARED INTERLAYERED CLAY MOLECULAR SIEVE PRODUCTS WITH REGULARLY INTERSTRATIFIED MINERAL STRUCTURE

BACKGROUND OF THE INVENTION

This invention relates to pillared interlayered clay molecular sieve (PICMS) products and methods of their preparation. These products can be used as hydrocarbon conversion catalysts, absorbents and catalyst carriers. More particularly, the present invention relates to cross-linked regularly interstratified mineral clay (RIMC) products and methods of their preparation.

Until now, prior PICMS products were all cross-linked smectites type molecular sieve products prepared from smectites clays. PICMS products prepared from clays other than smectites have never been reported in the literature.

The smetites is a type of single layer mineral clay which is represented by the general formula:

The smectites clay group includes motmorillonite, bentonite, beidellite, hectorite, vermiculite and the like. Their characteristic designation is basal spacing ($d_{001}$) of 9-15 Å for air dried samples.

The cross-linked smectites type PICMS products are prepared by insertion of organic cross-linking agent or inorganic polymeric cationic hydroxy metal complexes into interlayers of smectites and to prop open the two adjacent 2:1 clay layers of the swelling smectites. Thereby a unique internal micropore structure, surface area and catalytic activity are created.

Although the cross-linked smectites type PICMS products have the advantage of great versatility in adjusting pore size, high catalytic activity for cracking large molecule reactants and are simple to prepare, their thermal and hydrothermal stabilities are poor. Under the conditions of the thermal or hydrothermal treatment, the props which serve to prop open the adjacent 2:1 clay layers of the smectites could be removed from the original prop points and cause 2:1 clay layers to collapse. It is apparent that the disintegration of pillars or 2:1 clay layers structure will make the micropore structure, surface areas and catalytic activities to diminish drastically. According to the literature the organic cross-linked smectites prepared by reacting smectites with organic amines could hardly withstand a thermal treatment at 250°-550° C. (Shabtai et al, Proc. 6th Inter. Congr. Catal., B5, 1-7, 1976; U.S. Pat. No. 4,367,163). Inorganic cross-linked smectites prepared by reacting smectites with polymeric cationic hydroxy metal complexes could only withstand treatment at 550° C. (U.S. Pat. Nos. 4,216,188; 4,238,364).

In order to improve thermal and hydrothermal stabilities of cross-linked smectites type molecular sieve products, an improved method of preparing cross-linking agents were reported in the literature (U.S. Pat. Nos. 4,176,090; 4,248,739). Their thermal and hydrothermal stabilities were enhanced by said improved cross-linking agents, however the improvement is not good enough as the resulting product can only withstand treatment at 676° C. with 5 psi steam for 8 hours.

So far, the thermal and hydrothermal stabilities of the PICMS product prepared by smectite clays is still an open question. Sample treated at 730° C. with steam for 4 hours, 90 percent of its surface area and 80 percent of its pore volumes were lost. Its microactivities drop sharply from 80 percent to 30 percent (Occelli, M. L., I. and E.C. Prod. Res. and Dev., 22, 553, 1983).

All the data mentioned above have clearly indicated that the prior PICMS product is not as good as REY type zeolite catalysts with respect to high temperature stability in order to be used in catalytic cracking process. Hence no cracking catalysts from cross-linked smectites type PICMS products was ever used in commercial scale.

An object of the present invention is to develop another class of catalytic materials other than smectites and thereby to prepare a class of new PICMS with large pore size and excellent hydrothermal stability so as to improve the deficiency of prior PICMS of cross-linked smectites. Another object of the present invention is to provide the method of preparation and the application of said new PICMS.

SUMMARY OF THE INVENTION

The present invention provides a class of PICMS products with RIMC structure, such as cross-linked rectorites, mica/smectites, illite/smectites, glauconite/smectites, chlorite/smectites, vermiculite/smectites, kaolinite/smectites. The PICMS products comprises the unit layers which is actually the non-swelling component in the RIMC. The pillars made of inorganic oxides inserted into the interlayers of the swelling components in RIMC structure, and the micropores formed by the unit layers and the pillars.

The PICMS products have a basal spacing of 17.0-50.0 Å, which includes the basal spacing of a pair of swelling and non-swelling components. The layer thickness of not less than 17.0 Å and an interlayer distance of 0-33.0 Å. The pores with less than 50 Å in radius in said molecular sieve products comprise more than fifty per cent of its pore volume. They are a class of molecular sieves having large micropore size.

The present invention also provides a method of preparation of the said products. Specifically, the products of the present invention are prepared by reacting RIMC with the polymeric cationic hydroxy metal complex in aqueous solution.

Furthermore, the present invention provides applications of the said products. The products of present invention are useful as commercial catalysts and/or catalyst carriers for carbonium-ion type reactions such as catalytic cracking, hydrocracking, reforming, oligomerization and alkylation. They are also useful as adsorbents.

DETAILED DESCRIPTION OF THE PRESENT INVENTION

The present invention provides a class of PICMS made from the catalytic materials with the structure of RIMC such as cross-linked rectorites, -mica/smectites, -illite /smectites, -glauconite/smectites, -chlorite/smectites, -vermiculite /smectites, kaolinite/smectites.

The PICMS products comprises the unit layers which is actually the non-swelling component in the RIMC, the pillars made of inorganic oxides inserted into the interlayers of the swelling components in the RIMC structure, and the micropores formed by the unit layers and the pillars.

The RIMC consist of swelling and non-swelling components arranged in a manner that alternatively shareing a 2:1 clay layer which formed a regularly crystalline structure. It retains not only the characters of swelling single layer mineral clays, so that enables pillared interlayers could be formed, but also because of the existence of alternated arrangements between swelling and non-swelling component layers, it possesses specific characters over those of swelling single layer mineral clays.

Figure 1:
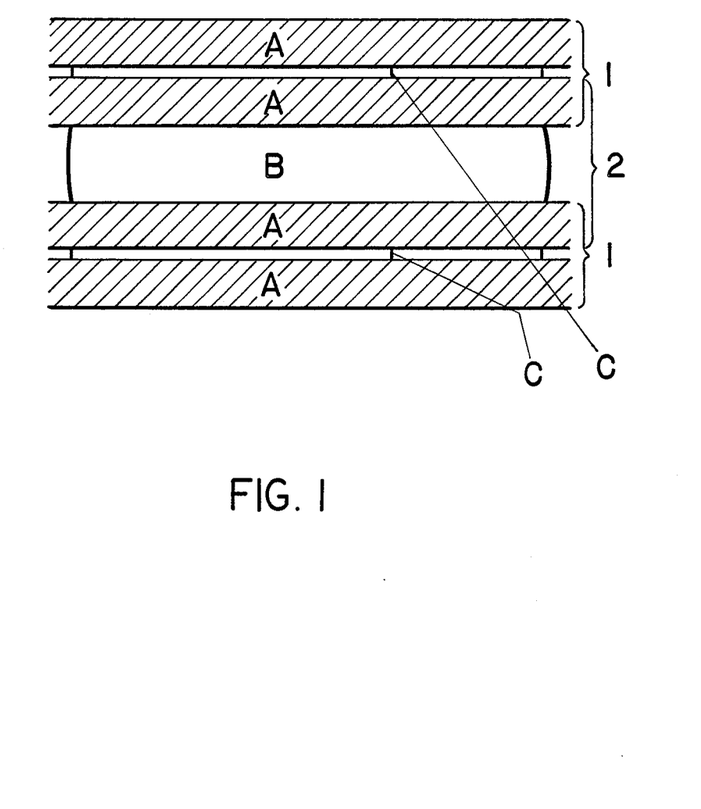
FIG. 1 represents a cross-sectional view of the structure of RIMC used by the present invention.

FIG. 1 is a cross-sectional view of the structure of the RIMC where designation 1 and 2 represent respectively non-swelling and swelling components. The designation A shows the 2:1 clay layers, B and C represent respectively exchangeable cations in the swelling component and the fixed cations in the non-swelling component in the RIMC structure.

The typical RIMC include a naturally occurring or synthetic rectorites, mica/smectites, illite/smectites, glauconite/smectites, chlorite/smectites(e.g. tosudit), mica/vermiculites, kaolinite/smectites RIMC and mixtures thereof. Said RIMC is fundamentally different from the single layer mineral clay (e.g. smectites) in the structure and the characters. They belong respectively to the different clay family. The said RIMC of this invention is characterized by interstratified mineral crystals regularly formed by alternately arranged between swelling and non-swelling components of the mineral clays. Its basal spacing is not less than 17.0 Å.

The character of the RIMC provided by the present invention are illustrated by the rectorites which is justified for 1:1 regular interstratification of dioctahedral mica and dioctahedral smectite.

The chemical structure formula of the rectorites (water free) are represented as follows:

$$\{(Na_{0.72}K_{0.02}Ca_{0.05})(Ca_{0.24}Na_{0.07})\}Al_{4.00}Mg_{0.02})^{VI}$$
fixed cations　　exchangeable　　six
　　　　　　　　　cations　　　coordinated
　　　　　　　　　　　　　　　　ions $$[Si_{6.58}Al_{1.62}]^{IV}O_{22}$$
four coordinated ions The main characters of the rectorites are narrated as follows:

1. The rectorite structure contains a swelling clay component part. On its 2:1 clay layers there are isomorphous substitutions. In its interlayer zones there are exchangeable cations. The swelling clay component part can be propped to form large micropores under substitution of cross-linked agent e.g. polymeric cationic hydroxy metal (Al or Zr) complex for exchangeable cations.

2. The 2:1 clay layers are shared by mica and smectites components in the rectorite structure. Thereof isomorphous substitutions occur on the tetrahedral silica-oxygen sheet in the 2:1 clay layers so as to form stable ionic bonds between exchangeable cations and the ions which are deficient in the positive charges on the 2:1 clay layers. Thus it is advantageous to form the stable connections of clay layers and the pillars.

3. The structure of the rectorites clay layers are stable under a temperature as high as 800° C. for 17 hours.

The present invention has found that the PICMS products prepared from RIMC with the characteristics of above said mineral clays have extraordinary thermal and hydrothermal stabilities.

The inorganic oxides inserted into the interlayers of the swelling component in RIMC consist essentially of alumina, zirconia and mixtures thereof. During the preparation process of the PICMS of present invention, the precursors of the inorganic oxides mentioned above are their relative polymeric cationic hydroxy metal complex, i.e. polymerized aluminum chlorohydroxide, polymerized zirconium chlorohydroxide and copolymers thereof or mixtures thereof. The polymerized aluminum chlorohydroxide has the general formula: $Al_{2+n}(OH)_{3n}Cl_6$ wherein n has a value of about 4 to 12 in general case. The polymerized zirconium chlorohydroxide possesses the following general formula: $[Zr_4(OH)_{12}(H_2O)_{12}]Cl_4$. Both polymers mentioned above can be obtained either from market or prepared by the art disclosed in the following references:

(a). H. W. Kohlschuter et al: Z. Anorg. Allgem. Chem., 248,319 (1941)

(b). Tsutida and Kobayashi: J. Chem.Soc.Japan (Pure Chem. Sec.), 64,1268(1943)

(c) T. G. Cwe Berg: Z. Anorg. Allgem. Chem.,269,213 (1952)

(d). Inove, Osugi and Kanaya: J. Chem. Soc.Japan (Ind. Chem. Sec.), 61,407 (1958)

(e). German Pat. No. 1,102,713

(f). A. Clearfield and P. A. Vaughan :Acta Cryst., 9, 555 (1956)

(g). G. M. Muha and P. A. Vaughan: J. Chem. Phys.,33,194–9 (1960)

(h). A. N. Ermakov, I. N. Marov, and V. K. Belyaeva: Zh. Neorgan. Khim.,8(7),1923 (1963)

The PICMS of present invention were prepared by cross-linking the clay slurry of the RIMC mentioned above with the solution of the polymeric cationic hydroxy metal complex mentioned above. The following general procedure may be used:

(a). The preparation of mineral clay slurry: The purified naturally occurring Ca-form mineral clay was changed into that of Na-, NH4- or RE-form by ion-exchange method and thereby the clay slurry with a solid content of less than 5% (wt.) and a particle size of smaller than 2μ is obtained.

(b). The preparation of the solution of polymeric cationic hydroxy metal complex (cross-linking reagent): The polymer was diluted with deionized $H_2O$ so as to obtain the aqueous solution of polymeric cationic hydroxy metal complex with a concentration of 10–1000, preferably 30–500 milligram-atom aluminum per liter or 5–100, preferably 10–50 milligram-atom zirconium per liter.

(c). The cross-linking reaction: The mineral clay slurry prepared as mentioned above was added to cross-linking reagent at a ratio of 1.5–5.0 milligram-atom aluminum or 2.0–5.0 milligram-atom zirconium per gram clay (dry basis). The reaction proceeds under stirring at the temperature ranging from room temperature to 100° C. for more than 5 minutes. During the reaction the pH of said mixture is adjusted with $NH_4OH$ and kept within the range of 4–6.

(d). Ageing: The resulting product was stilled and aged, with a pH of 4–6 at the temperature ranging from room temperature to 75° C. for 0–24 hours.

(e). Filtering and washing: After filtering, the filtered cake was washed with deionized $H_2O$ until $Cl^-$ in filtrate was undetectable.

(f). Drying: The washed filtered cake was dried at the temperature ranging from room temperature to 300° C.

(g). Calcining: The dried filtered cake was calcined at 550°–750° C. for 2–5 hours so as to convert the polymeric cationic hydroxy metal complex into oxides and thereby the PICMS of present invention was obtained.

Figure 2:
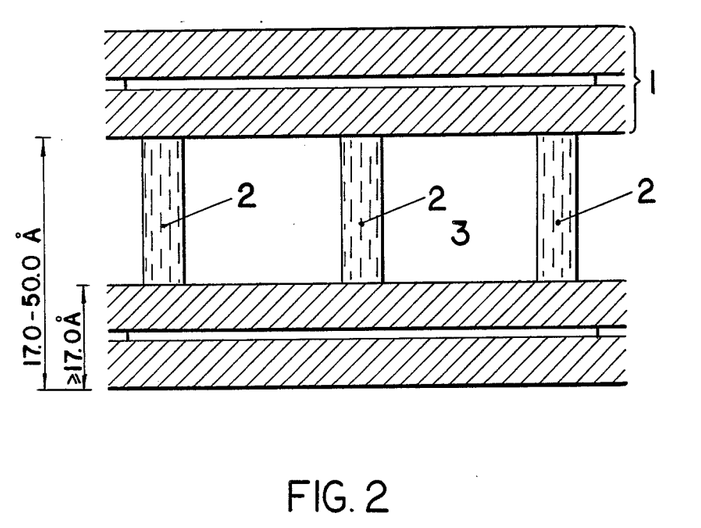
FIG. 2 is a cross-sectional view of the structure of the PICMS products provided by the present invention.

FIG. 2 is a scheme of PICMS with RIMC structure of present invention. Wherein 1 is the unit layer of the PICMS of present invention, which is actually a non-swelling component in the RIMC. 2 is the pillars of the PICMS of present invention, which is made of inorganic oxides converted from the polymeric cationic hydroxy metal complex inserted into the interlayer of swelling component in the RIMC. 3 is the pores of the PICMS of present invention, which is established by introducing into the RIMC inorganic oxide pillars which is discrete/non-continuous and vertical with neighbouring layers.

The structural characteristics of the PICMS (fresh) of present invention are as follows: they possess a layer thickness of not less than 17.0 Å, a (001) basal spacing of 17.0–50.0 Å, an interlayer distance of 0–33.0 Å, and have greater than 50% of its pore volume in pores of less than 50.0 Å in radius.

The structural characteristics of the PICMS (fresh) of cross-linked rectorite type in present invention are as follows: they possess a layer thickness of 20.0–21.0 Å, a (001) basal spacing of 27.0–31.0 Å, an interlayer distance of 6.0–10.0 Å, and have greater than 50% of its pore volume in pores of less than 50.0 Å in radius.

The PICMS of present invention have the characteristics of a microporous structure and a solid acid sites, and are suitable for catalysts, used in carbonium-ion reactions, adsorbents and carriers. More particularly, the PICMS cross-linked rectorites in present invention and the products thereof possess not only the characteristics mentioned above but also have extraordinary thermal and hydrothermal stability which are far superior to that of the prior PICMS of cross-linked smectites type and also better than that of some commercial REY-type zeolite catalysts. After hydrothermal treatment at 800° C. under atmospheric pressure with 100% steam for 17 hours, said PICMS remain essentially the constant structure and the constant interlayer distance. It retains a surface area of 70%, MAT conversion of 90%. Furthermore, the PICMS of cross-linked rectorites in present invention are benificial to crack heavy feedstocks and are especially suitable for preparation of cracking catalysts for petroleum processing.

The PICMS of present invention may be combined with other inorganic oxide adsorbents and catalysts such as silica, alumina, silica-magnesia, silica-alumina hydrogel or hydrosol, and natural or synthetic zeolites, and clays. Said PICMS are particularly useful in the preparation of catalysts which contain active/stabilizing metals such as platinum, palladium, cobalt, molybdenum, nickel, tungsten, rare-earths and so forth, as well as matrix components such as silica, alumina and silica-alumina hydrogel. These catalysts are used in conventional petroleum conversion processes such as catalytic cracking, hydrocracking, reforming, oligomerization, alkylation and isomerization and as molecular sieves adsorbents, carriers.

The following specific examples will give a further illustration of present invention but not limit the scope of present invention.

EXAMPLE 1

The Na-form rectorite clay slurry was prepared by stirring a mixture of 1 Kg naturally occurring Ca-form rectorite clay with 20 Kg of deionized $H_2O$ and 3 Kg of strong acidic cation exchange resin of styrene in sodium type which has an exchange capacity of 4 milligram equivalent per gram for 8 hours and stand overnight. The clay slurry of particle size smaller than $2\mu$ was separated out by floatation. The solid content of this slurry was 2.29% (wt.). The polymerized aluminum chlorohydroxide cross-linking reagent with a concentration of 33.3 milligram-atom aluminum per liter was prepared by reacting 0.2 mole NaOH with 0.2 mole $AlCl_3$ and aged for 6 days at room temperature, then diluting with equal volume of $H_2O$. The clay slurry was added to the polymerized aluminum chlorohydroxide aqueous solution with a ratio of 3.29 milligram-atom aluminum per gram clay (dry basis). The said mixture was reacted at room temperature with stirring for about 0.5 hour. During the reaction the pH of the solution was adjusted with 3% $NH_4OH$ and kept within the range of 4–6. Then the resulting mixture was aged for 24 hours at room temperature. The pH was maintained at 4–6, filtered, washed to be free of $Cl^-$, dried at 110° C., calcined in air for 2 hours at 650° C., thereby the PICMS with $Al_2O_3$ pillars of cross-linked rectorites type were obtained.

The structure characteristics of said molecular sieves measured by conventional X-ray powder diffraction method are as follows: they possess a layer thickness of 20.0–21.0 Å, a (001) basal spacing of 27.0–31.0 Å with various water content, and an interlayer distance of 6.0–10.0 Å. The major components of said molecular sieves measured by standard chemical analysis is listed in Table 1. The surface areas, pore volumes and distributions of said molecular sieves measured by BET low temperature $N_2$ adsorption method are listed in Table 2.

TABLE 1

| Major components | $Na_2O$ | $Fe_2O_3$ | $Al_2O_3$ | $SiO_2$ |
|---|---|---|---|---|
| Content, % (wt.) | 1.3–2.0 | 0.29 | 45.5 | 47.6 |

TABLE 2

| Sample | Item | | | | | |
|---|---|---|---|---|---|---|
| | Surface area (BET), $m^2/g$ | Pore volume (BET), ml/g | Pore distribution | | | |
| | | | 50 Å | 50–100 Å | 100–150 Å | 150–200 Å |
| Fresh | 174 | 0.17 | 66.9 | 22.8 | 9.7 | 0.6 |
| After treatment at 800° C. with 100% | 129 | 0.20 | 43.8 | 21.5 | 15.9 | 18.8 |

TABLE 2-continued

| Sample | Item | | | | | |
|---|---|---|---|---|---|---|
| | Surface area (BET), m²/g | Pore volume (BET), ml/g | Pore distribution | | | |
| | | | 50 Å | 50–100 Å | 100–150 Å | 150–200 Å |
| steam under atmosphere for 17 hours | | | | | | |

EXAMPLE 2

The PICMS of cross-linked rectorites type prepared by the method in Example 1 have excellent thermal stability compared with that of cross-linked smectites type.

Figure 3:
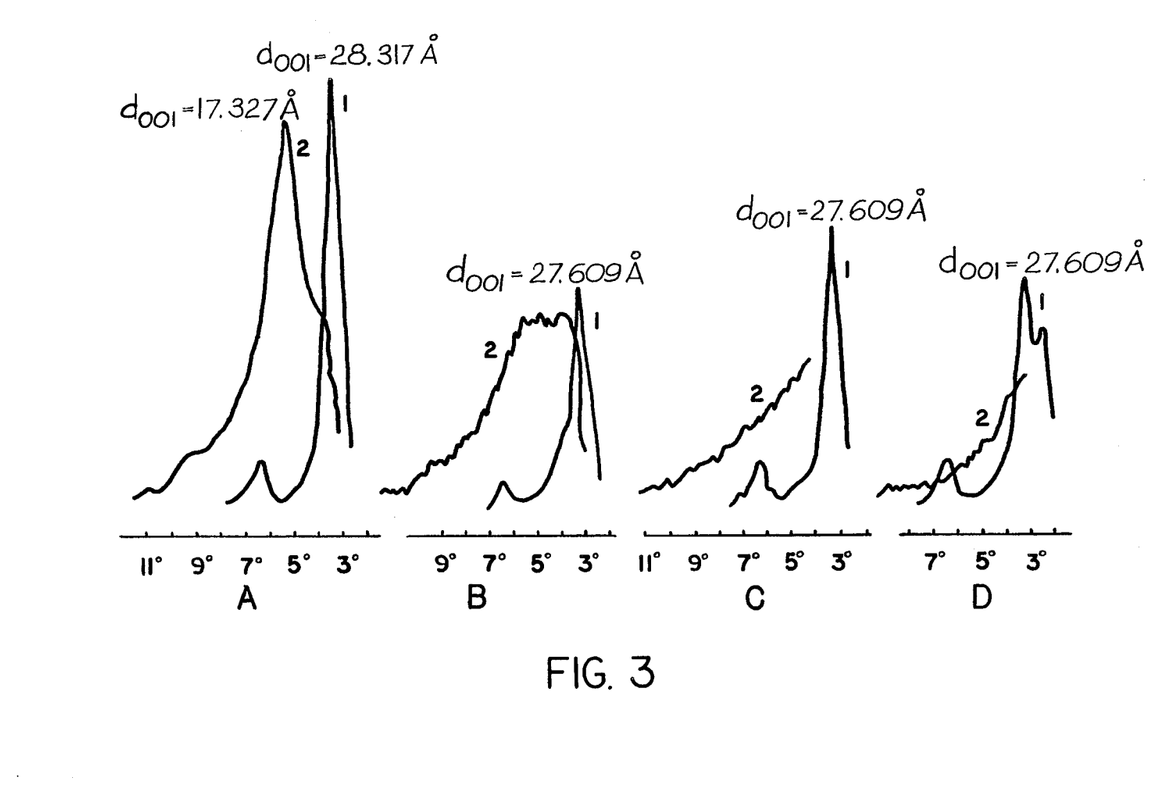
FIG. 3 shows X-ray powder diffraction patterns (001) of cross-linked rectorites and cross-linked smectites after thermal treatment at different temperatures.

FIG. 3 shows X-ray powder diffraction patterns (001) of the PICMS of cross-linked rectorites and that of cross-linked smectites after thermal treatment at different temperatures. The measurement was made with X-ray powder diffratometer of Geigerflex D-9C model, which is made in Japan. The measurement conditions were as follows: $CuK_\alpha$ radiation, Ni filter, scintillation counter, slit system of 1°, 0.3°, 1°. In FIG. 3, 1 and 2 represent respectively the X-ray powder diffraction patterns of the PICMS of cross-linked rectorites and that of cross-linked smectites. In this figure, A, B, C and D represent respectively the patterns of fresh sample, sample after treatment at 550° C. for 2 hours, sample after treatment at 750° C. for 2 hours and sample after treatment at 800° C. for 17 hours. It can be seen from the figure that crystal structure of the PICMS of cross-linked smectites after 2 hrs. treatment at 550° C. has collapsed, whereas the cross-linked rectorites retained its crystal structure after treatment at 800° C. for 17 hours.

EXAMPLE 3

The PICMS of cross-linked rectorites type prepared by the method in Example 1 have excellent hydrothermal stability compared with that of the PICMS of cross-linked smectites, amorphous silica-alumina cracking catalysts and commercial REY-type zeolite cracking catalysts.

Figure 4:
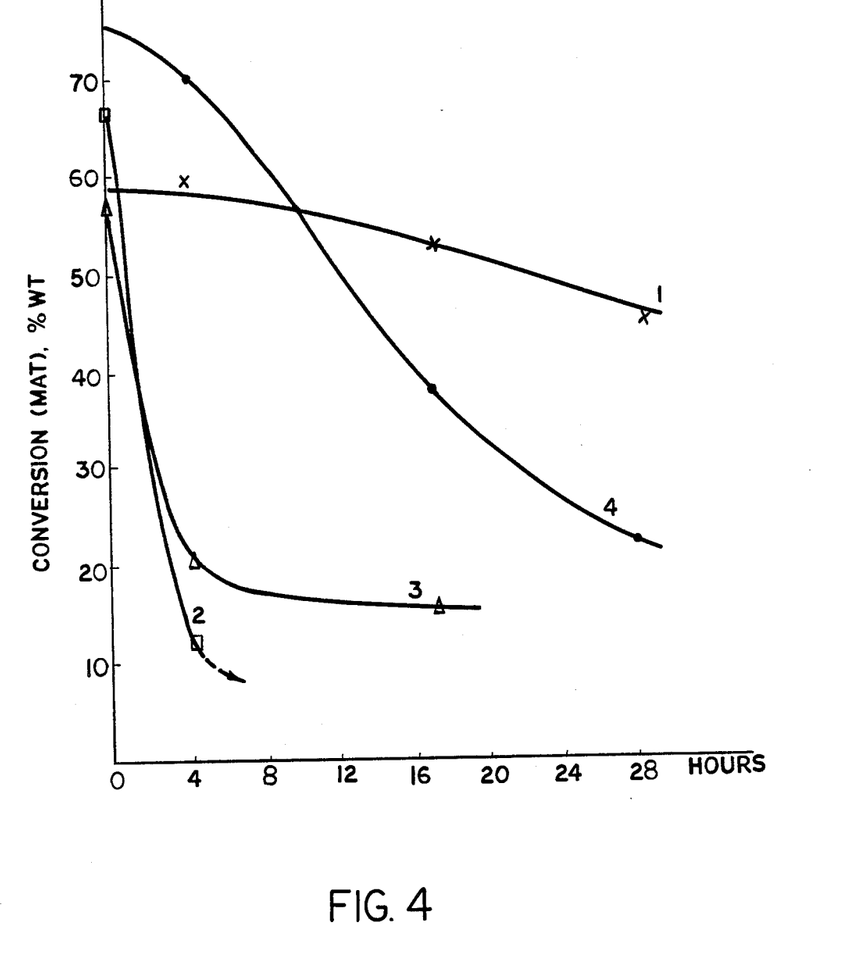
FIG. 4 shows the microactivity curves of the PICMS of cross-linked rectorites, PICMS of cross-linked smectites, amorphous silica-alumina catalysts containing 13 percent alumina and commercial REY zeolite cracking catalysts after hydrothermal treatment with 100 per cent steam at atmospheric pressure and various temperatures.

FIG. 4 shows the comparison of the conversion (MAT) of these four samples after hydrothermaly treated with 100% steam under 1 atm. at various temperatures for light diesel feedstock. The evaluation test was carried out in a MAT unit. The evaluation conditions were as follows:reactant: Dagang light diesel oil (235°–337° C.), reaction temperature: 460° C., contact time: 70 seconds, WHSV: 16 hr.$^{-1}$, catalyst-to-oil ratio: 3.2, sample used: 5 g. In FIG. 4, curve 1,2,3 and 4 represent respectively the decline in activities of the PICMS of cross-linked rectorites, the PICMS of cross-linked smectites, amorphous silica-alumina cracking catalysts and commercial REY-type zeolite cracking catalysts.

FIG. 4 shows that the microactivity of the PICMS of cross-linked rectorites retains a value of 46%, while that of the commercial REY-type zeolite cracking catalysts declines to a value of 23% after the hydrothermal treatment at 800° C. with 100% steam for 28 hours. Furthermore, the microactivity of the PICMS of cross-linked smectites and amorphous silica-alumina cracking catalysts have dropped sharply to values of 12% and 20% respectively after the hydrothermal treatment at 800° C. with 100% steam for 4 hours.

EXAMPLE 4

The PICMS of cross-linked rectorite type prepared by the method in Example 1 is capable to resist contaminations of heavy metals.

The conventional REY-type zeolite and the PICMS of cross-linked rectorites were impregnated respectively with $NH_4VO_3$ Aqueous solution at the ratio (wt./wt.) of 1:0.001:1 (sample:$V:H_2O$) and 1:0.005:1 (sample:$V:H_2O$) at room temperature. Then the impregnated samples were dried at 120° C., the contaminated samples containing 1000 ppm and 5000 ppm vanadium respectively were obtained. The cracking microactivities for light diesel feedstock of these contaminated samples after hydrothermal treatment at 800° C. with 100% steam under 1 atm. for 4 hours were evaluated respectively by the method in Example 3.

The results show that the percentage of the microactivity retention for the PICMS of cross-linked rectorites is far higher than that of the conventional REY-type zeolite after the same degree of contamination and the same severity of treatments. The data are listed in Table 3.

TABLE 3

| Sample | Item | | | |
|---|---|---|---|---|
| | $Na_2O$ content % (wt.) | Initial micro activity before contamination, % (wt.) | Microactivity after treatment and contamination % (wt.) | Percentage of the microactivity retention % |
| | Contaminating vanadium to 1000 ppm | | | |
| PICMS of crosslinked rectorites | 2.00 | 62 | 56 | 90 |
| Conventional REY-type zeolite | 1.45 | 100 | 31 | 31 |
| | Contaminating vanadium to 5000 ppm | | | |
| PICMS of crosslinked rectorites | 2.00 | 62 | 46 | 74 |
| Conventional REY-type zeolite | 0.76 | 100 | 65 | 65 |

EXAMPLE 5

The cracking catalyst with an active component of PICMS of cross-linked rectorites has higher reactivity in cracking heavy distillate than the commercial REY-type zeolite cracking catalyst.

The mixture of the Na- form rectorite clay slurry prepared in Example 1 and Suzhou machine-selected 2# halloysite was slurried at a weight ratio of 1:1 (dry basis). After perfectly mixing by stirring the cross-linking reaction was proceeded in the way of Example 1 (the used weight of cross-linking reagent was based on the weight of rectorite), then aged, filtered, washed, spray dried, calcined by the method in Example 1, thereby the microspheric cracking catalyst containing the PICMS of cross-linked rectorites was obtained.

The cracking activities for light diesel feedstock and heavy distillate of the commercial REY-type zeolite cracking catalyst and the cracking catalyst containing the PICMS of cross-linked rectorites after the hydrothermal treatment at 800° C. with 100% steam under 1 atm for 17 hours were evaluated respectively. The MAT conversion data were obtained in the way of Example 3. The evaluation test for heavy distillate was carried out in a pilot fixed fluidized bed reactor. The test conditions were as follows: reactant: Dagang 330°–520° C. distillate, reaction temperature:450° C., contact time: 60 seconds, WHSV: 20 hr$^{-1}$, catalyst-to-oil ratio: 3.2, catalyst used: 100 g.

The evaluation data show that the conversion of heavy distillate with the cracking catalyst containing the PICMS of cross-linked rectorites is higher than that with the commercial REY-type zeolite cracking catalyst. The data are listed in Table 4.

TABLE 4

| | Catalyst after treatment | |
|---|---|---|
| | Cracking catalyst containing the PICMS of cross-linked rectorites | Commercial REY-type zeolite cracking catalyst |
| Reactant | Conversion, % (wt.) | |
| 235–337° C. distillate | 59 | 61 |
| 330–520° C. distillate | 68 | 59 |

EXAMPLE 6

The cracking catalyst containing the PICMS of cross-linked rectorites prepared by the method in Example 5 demonstrate similar selectivity in cracking a feedstock of mixed distillate-residue to that of the commercial REY-type zeolite cracking catalyst.

The selectivities of the commercial REY-type zeolite cracking catalyst and the cracking catalyst containing the PICMS of cross-linked rectorites after the hydrothermal treatment at 800° C. with 100% steam under 1 atm for 10 hours were evaluated respectively in a pilot fixed fluidized bed reactor. The evaluation conditions were as follows: reactant: mixture of 40% (wt.) Da-Gang 330°–520° C. distillate with 60% (wt.) Sheng-Li atmospheric residue therein the Conradson carbon residue content is 6.85% (wt.), reaction temperature: 500° C., reaction period: 230 seconds, WHSV: 10 hr.$^{-1}$, catalyst-to-oil ratio: 1.6, catalyst used: 20 g. The data are listed in Table 5.

TABLE 5

| | Item | | | | | |
|---|---|---|---|---|---|---|
| | Conversion, % (wt.) | | | | Light cycle oil yield, % (wt.) | Total conversion, % (wt.) |
| Catalyst | Diesel | Gasoline | Gas | Coke | | |
| Cracking catalyst containing the PICMS of cross-linked rectorites | 20.83 | 18.04 | 5.79 | 5.70 | 38.87 | 57.28 |
| Commercial REY-type zeolite cracking catalyst | 21.62 | 18.50 | 7.76 | 4.96 | 39.87 | 60.08 |

EXAMPLE 7

The PICMS of cross-linked rectorites type prepared by the method of Example 1 possess higher activity for oligomerization of olefins than that of the conventional amorphous silica-alumina catalyst.

The evaluation test was carried out on a micro-reactor with pulse technique. The evaluation conditions were as follows: reactant: propene (purity more than 99%), reaction temperature: 240° C., reaction pressure: 0.4 kg/cm$^2$, carrier gas: hydrogen (purity 99.999%), contact time: 0.5 seconds, sample used: 0.06 ml.

Under the same conditions indicated above, the initial conversion of the PICMS of cross-linked rectorites and the conventional amorphous silica-alumina catalyst for the oligomerization are 30% and 20% respectively.

EXAMPLE 8

The PICMS of cross-linked mica-montmorillonites type were prepared from mica-montmorillonite by the method in Example 1. The structure characteristics of said molecular sieves measured by conventional X-ray powder diffraction method are as follows: They possess a layer thickness of 20.0–21.0 Å, a (001) basal spacing of 29.5 Å (a basal spacing of 24.5 Å before cross-linking), and an interlayer distance of 7.5–8.5 Å. After the thermal treatment at 800° C. for 4 hours the (001) basal spacing decreased only slightly to 27.3 Å. Thereby it is concluded that said molecular sieves have good thermal stability.

EXAMPLE 9

The PICMS of cross-linked chlorite-smectites type were prepared from chlorite-smectite by the method in Example 1. The structure characteristics of said molecular sieves measured by conventional X-ray powder diffraction method are as follows: they possess a layer thickness of 23.0–24.0 Å, a (001) basal spacing of 32.0 Å (a basal spacing of 28.0 Å before cross-linking), and an interlayer distance of 8.0–10.0 Å.

EXAMPLE 10

The polymerized zirconium chlorhydroxide cross-linking reagent was prepared by polymerizing 0.33 mole ZrOCl$_2$ in itself with refluxing under 1 atm at boiling temperature for 20.5 hours, then 120 ml of this polymer was taken out and diluted with 1530 ml of deionized H$_2$O. 436.7 g of the rectorite clay slurry prepared in Example 1 was added to the diluted polymerized zirconium chlorhydroxide aqueous solution mentioned above. Said mixture was reacted, aged, filtered, washed, dried and calcined in the way of that in Example 1 and thereby the PICMS with ZrO$_2$ pillars of cross-linked rectorites type were obtained.

The structure characteristics of said molecular sieves measured by conventional X-ray powder diffraction method are as follows: they possess a layer thickness of 20.0–21.0 Å, a (001) basal spacing of 30.0 Å, and an interlayer distance of 9.0–10.0 Å. The initial microactivity (MAT) of said molecular sieves evaluated by the method in Example 3 was 37% (wt.).

EXAMPLE 11

The PICMS of cross-linked rectorites type prepared with the polymerized aluminum chlorhydroxide cross-linking reagent containing silicon also have excellent hydrothermal stability.

The said molecular sieves can be prepared as follows:

(1) The preparation of aluminum polymers: 9.4 ml of aluminum polymers with a concentration of 6.99 gram-atom aluminum per liter prepared by reacting chlorhydric acid with an excess of metallic aluminum were diluted with 977 ml of deionized H$_2$O. The pH of the diluted polymers solution was adjusted with 3% NH$_4$OH and kept within the range of 4–6.

(2) The preparation of silicon hydrosol: 1.9 gram of Na$_2$SiO$_3$ sol with a SiO$_2$ content of 30% (wt.) and a SiO$_2$/Na$_2$O ratio of 3.0 was diluted to 100 ml with deionized H$_2$O. A diluted chlorhydric acid solution obtained by diluting 1 ml of 37% HCl to 100 ml with deionized H$_2$O was added to the diluted Na$_2$SiO$_3$ sol mentioned above, thereby a silicon sol with a pH of 3–5 was obtained.

(3) The preparation of the solution of cross-linking reagent: The clear and colorless solution of aluminum cross-linking reagent containing silicon was obtained by mixing aluminum polymers with silicon hydrosol prepared above, adjusting the pH of said mixture with 3% NH$_4$OH and keeping within the range of 4–6, then ageing at room temperature for 24 hours.

(4) The preparetion of molecular sieves: 873.4 g of the rectorite clay slurry prepared in Example 1 was added to the solution of aluminum cross-linking reagent containing silicon prepared above. The mixture was reacted, aged, filtered, washed, dried and calcined in the way of that in Example 1 and thereby the PICMS with SiO$_2$—Al$_2$O$_3$ pillars of cross-linked rectorites type were obtained.

A (001) basal spacing of 27.0–30.0 Å was measured by conventional X-ray powder diffraction method. By the evaluation method in Example 3, the initial microactivity (MAT) was 61% (wt.) and decreased to 40% (wt.) after the hydrothermal treatment at 800° C. with 100% steam under 1 atm for 17 hours.

EXAMPLE 12

The PICMS of present invention can be also prepared by using polymerized aluminum chlorohydroxide containing boron as the cross-linking reagent.

9.4 ml of aluminum polymers with a concentration of 6.99 gram-atom aluminum per litre prepared by reacting chlorhydric acid with an excess of metallic aluminum were diluted upto a concentration of 252.8 milligram-atom per liter with deionized H$_2$O. The chemically pure Na$_2$B$_4$O$_7$·10 H$_2$O of a calculated amount was added to the diluted aluminum polymers mentioned above at a ratio of 0.1 milligram-mole Na$_2$B$_4$O$_7$·10H$_2$O per milligram-atom aluminum. The solution of aluminum cross-linking reagent containing boron was obtained by adjusting the pH of the mixture prepared above with 3% NH$_4$OH and keeping within a range of 4–6, then ageing at room temperature for 24 hours. 873.4 g of the rectorite clay slurry prepared in Example 1 was added to the solution of aluminum cross-linking reagent containing boron prepared above. Said mixture was reacted, aged, filtered, washed, dried and calcined in the way of that in Example 1 and thereby the PICMS with the pillars containing B$_2$O$_3$—Al$_2$O$_3$ of cross-linked rectorites type were obtained.

A (001) basal spacing of 27.0–30.0 Å was measured by conventional X-ray powder diffraction method. By the evaluation method in Example 3, the initial microactivity (MAT) was 65% (wt.).

We claim:

1. A class of pillared interlayered clay molecular sieves consisting of the unit layers which is actually the non-swelling component in the regularly interstratified mineral clays and the pillars made of inorganic oxides inserted into the interlayers of the swelling component in said regularly interstratified mineral clay.

2. The molecular sieves of claim 1 wherein said regularly interstratified mineral clay are selected from the naturally occurring or chemically synthesized group consisting of mica-smectite, illite-smectite, glauconite-smectite, chlorite-smectite, mica-vermiculite, kaolinite-smectite and mixtrures thereof.

3. The molecular sieves of claim 1 wherein said regularly interstratified mineral clay are naturally occurring or synthetic rectorite or mixtures thereof.

4. The molecular sieves of claim 1 wherein said inorganic oxides inserted into the interlayers of the swelling component in the regularly interstratified mineral clay are selected from the group consisting of alumina, zirconia and mixtures thereof.

5. The molecular sieves of claim 3 wherein said inorganic oxides inserted into the interlayers of the swelling component in the regularly interstratified mineral clay are selected from the group consisting of alumina, zirconia and mixtures thereof.

6. The molecular sieves of claim 1 which possesses a layer thickness of not less than 17.0 Å, a (001) basal spacing of 17.0–50.0 Å, an interlayer distance of 0–33.0 Å and have greater than 50% of its pore volume in pores of less than 50.0 Å in radius.

7. The molecular sieves of claim 3 which possesses a layer thickness of 20.0–21.0 Å, a (001) basal spacing of 27.0–31.0 Å, an interlayer distance of 6.0–10.0 Å and have greater than 50% of its pore volume in pores of less than 50.0 Å in radius.

8. A process for preparing the pillared interlayered clay molecular sieves which comprises cross-linking a slurry of the regularly interstratified mineral clay with a solution of the polymeric cationic hydroxy metal complex.

9. The process of claim 8 wherein said regularly interstratified mineral clay are selected from the naturally occurring or synthetic group consisting of mica-smectite, illite-smectite, glauconite-smectite, chlorite-smectite, mica-vermiculite, kaolinite-smectite and mixtures thereof.

10. The process of claim 8 wherein said regularly interstratified mineral clay are naturally occurring or synthetic rectorite or mixtures thereof.

11. The process of claim 8 wherein said polymeric cationic hydroxy metal complex are selected from the group consisting of polymerized aluminum chlorohydroxide, polymerized zirconium chlorohydroxide and copolymers thereof or mixtures thereof.

12. The process of claim 10 wherein said polymeric cationic hydroxy metal complex are selected from the group consisting of polymerized aluminum chlorohydroxide, polymerized zirconium chlorohydroxide and copolymers thereof or mixtures thereof.

13. The process of claim 8 which comprises:
(a). changing the naturally occurring mineral clay from Caform into Na-, NH$_4$- or RE- form followed by preparing the clay slurry of particle size smaller than 2μ with a solid content of less than 5% (wt.);
(b). preparing the aqueous solution of polymeric cationic hydroxy metal complex with a concentration of 10–1000, preferably 30–500 milligram-atom aluminum per liter or 5–100, preferably 10–50 milligram-atom zirconium per liter;
(c). cross-linking the clay slurry with the aqueous solution of polymeric cationic hydroxy metal complex at a ratio of 1.5–5.0 milligramatom aluminium or 2.0–5.0 milligram-atom zirconium per gram clay (dry basis) at the temperature ranging from room temperature to 100° C. with stirring for more than 5 minutes and adjusting the PH of said mixture with NH$_4$OH and keeping it within the range of 4–6 during the reaction process;

(d). ageing by standing at room temperature to 75° C. for 0–24 hours with the PH range of 4–6; and (e). filtering, washing, drying and calcining.

14. An adsorbent composition comprising the pillared interlayered clay molecular sieves of claim 1.

15. A carrier composition comprising the pillared interlayered clay molecular sieves of claim 1.

16. A pillared interlayed clay molecular sieve as in claim 1, wherein the clay layers are stable for 17 hours at a temperature of 800° C.

17. A pillared interlayed clay molecular sieve as in claim 7, wherein the clay layers are stable for 17 hours at a temperature of 800° C.

18. A process, as in claim 13, wherein said pillared interlayed clay molecular sieve is stable 17 hours at a temperature of 800° C.

* * * * *